(12) United States Patent
Altmann et al.

(10) Patent No.: US 10,939,871 B2
(45) Date of Patent: *Mar. 9, 2021

(54) BASKET CATHETER WITH MICROELECTRODE ARRAY DISTAL TIP

(71) Applicant: Biosense Webster (Israel) Ltd., Yokneam (IL)

(72) Inventors: Andres Claudio Altmann, Haifa (IL); Assaf Govari, Haifa (IL); Christopher Thomas Beeckler, Brea, CA (US); Rowan Olund Hettel, Pasadena, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/680,269

(22) Filed: Nov. 11, 2019

(65) Prior Publication Data

US 2020/0077959 A1 Mar. 12, 2020

Related U.S. Application Data

(63) Continuation of application No. 16/054,715, filed on Aug. 3, 2018, now Pat. No. 10,470,714, which is a (Continued)

(51) Int. Cl.
*A61B 5/042* (2006.01)
*A61B 18/14* (2006.01)
(Continued)

(52) U.S. Cl.
CPC .......... *A61B 5/6858* (2013.01); *A61B 5/0422* (2013.01); *A61B 5/6851* (2013.01); (Continued)

(58) Field of Classification Search
CPC .... A61B 5/0422; A61B 5/6858; A61B 5/6859
See application file for complete search history.

(56) References Cited

U.S. PATENT DOCUMENTS

| 5,391,199 A | 2/1995 | Ben-Haim |
| 5,443,489 A | 8/1995 | Ben-Haim |
| (Continued) | | |

FOREIGN PATENT DOCUMENTS

| EP | 0965302 A2 | 12/1999 |
| WO | WO9502995 A1 | 2/1995 |
| (Continued) | | |

OTHER PUBLICATIONS

Extended European Search Report dated Sep. 5, 2016, issued in EP 16171704.6, 6 pages.

*Primary Examiner* — Lee S Cohen
(74) *Attorney, Agent, or Firm* — Lewis Roca Rothgerber Christie LLP

(57) ABSTRACT

A catheter adapted for greater mapping resolution and location precision has a basket-shaped, high density electrode assembly for large-area mapping, and an integrated distal tip providing an array of ultra-high density microelectrodes for acute focal mapping. The basket-shaped electrode assembly 18 has a plurality of electrode-carrying spines and the distal tip has a nonmetallic, electrically insulating substrate body with indentations in which microelectrodes are positioned in a manner that the outer surface is generally flush with the outer surface of the substrate body to present a generally smooth, atraumatic distal tip profile.

20 Claims, 12 Drawing Sheets

Related U.S. Application Data continuation of application No. 15/641,182, filed on Jul. 3, 2017, now Pat. No. 10,039,494, which is a continuation of application No. 15/132,198, filed on Apr. 18, 2016, now Pat. No. 9,693,733, which is a continuation of application No. 14/526,394, filed on Oct. 28, 2014, now Pat. No. 9,314,208.

(51) Int. Cl.
    *A61B 5/00*     (2006.01)
    *A61M 25/01*     (2006.01)
    *A61M 25/09*     (2006.01)
    *A61B 18/00*     (2006.01)
    *A61B 34/20*     (2016.01)
    *A61B 90/00*     (2016.01)
    *A61B 17/00*     (2006.01)

(52) U.S. Cl.
    CPC ........ *A61B 5/6859* (2013.01); *A61B 18/1492* (2013.01); *A61M 25/0147* (2013.01); *A61M 25/09* (2013.01); *A61B 2017/00053* (2013.01); *A61B 2018/00267* (2013.01); *A61B 2018/00351* (2013.01); *A61B 2018/00357* (2013.01); *A61B 2018/00577* (2013.01); *A61B 2018/1465* (2013.01); *A61B 2018/1467* (2013.01); *A61B 2034/2051* (2016.02); *A61B 2090/3954* (2016.02); *A61M 2025/0177* (2013.01)

(56) References Cited

U.S. PATENT DOCUMENTS

| | | | |
|---|---|---|---|
| 5,480,422 | A | 1/1996 | Ben-Haim |
| 5,546,951 | A | 8/1996 | Ben-Haim |
| 5,558,091 | A | 9/1996 | Acker et al. |
| 5,568,809 | A | 10/1996 | Ben-haim |
| 5,772,590 | A | 6/1998 | Webster, Jr. |
| 5,836,875 | A | 11/1998 | Webster, Jr. |
| 5,938,694 | A | 8/1999 | Jaraczewski et al. |
| 6,024,739 | A | 2/2000 | Ponzi et al. |
| 6,064,905 | A | 5/2000 | Webster, Jr. et al. |
| 6,748,255 | B2 | 6/2004 | Fuimaono et al. |
| 6,973,340 | B2 | 12/2005 | Fuimaono et al. |
| 7,818,048 | B2 | 10/2010 | Plaza |
| 8,133,220 | B2 | 3/2012 | Lee et al. |
| 8,414,579 | B2 | 4/2013 | Kim et al. |
| 8,588,886 | B2 | 11/2013 | de la Rama et al. |
| 9,314,208 | B1 | 4/2016 | Altmann et al. |
| 9,693,733 | B2 | 7/2017 | Altmann et al. |
| 10,039,494 | B2 | 8/2018 | Altmann et al. |
| 10,470,714 | B2 * | 11/2019 | Altmann ............... A61B 5/6859 |
| 2004/0092806 | A1 | 5/2004 | Sagon et al. |
| 2005/0187456 | A1 | 8/2005 | Rashidi |
| 2006/0100669 | A1 | 5/2006 | Fuimaono et al. |
| 2008/0243214 | A1 | 10/2008 | Koblish |
| 2010/0168557 | A1 | 7/2010 | Deno et al. |
| 2012/0203316 | A1 | 8/2012 | Moffitt et al. |
| 2013/0123775 | A1 | 5/2013 | Grunewald et al. |
| 2014/0257069 | A1 | 9/2014 | Eliason et al. |
| 2014/0305699 | A1 | 10/2014 | Govari |
| 2014/0309512 | A1 | 10/2014 | Govari et al. |
| 2015/0080693 | A1 | 3/2015 | Solis |

FOREIGN PATENT DOCUMENTS

| | | |
|---|---|---|
| WO | WO9605768 A1 | 2/1996 |
| WO | 9724983 A2 | 7/1997 |
| WO | 9829033 A1 | 7/1998 |

\* cited by examiner

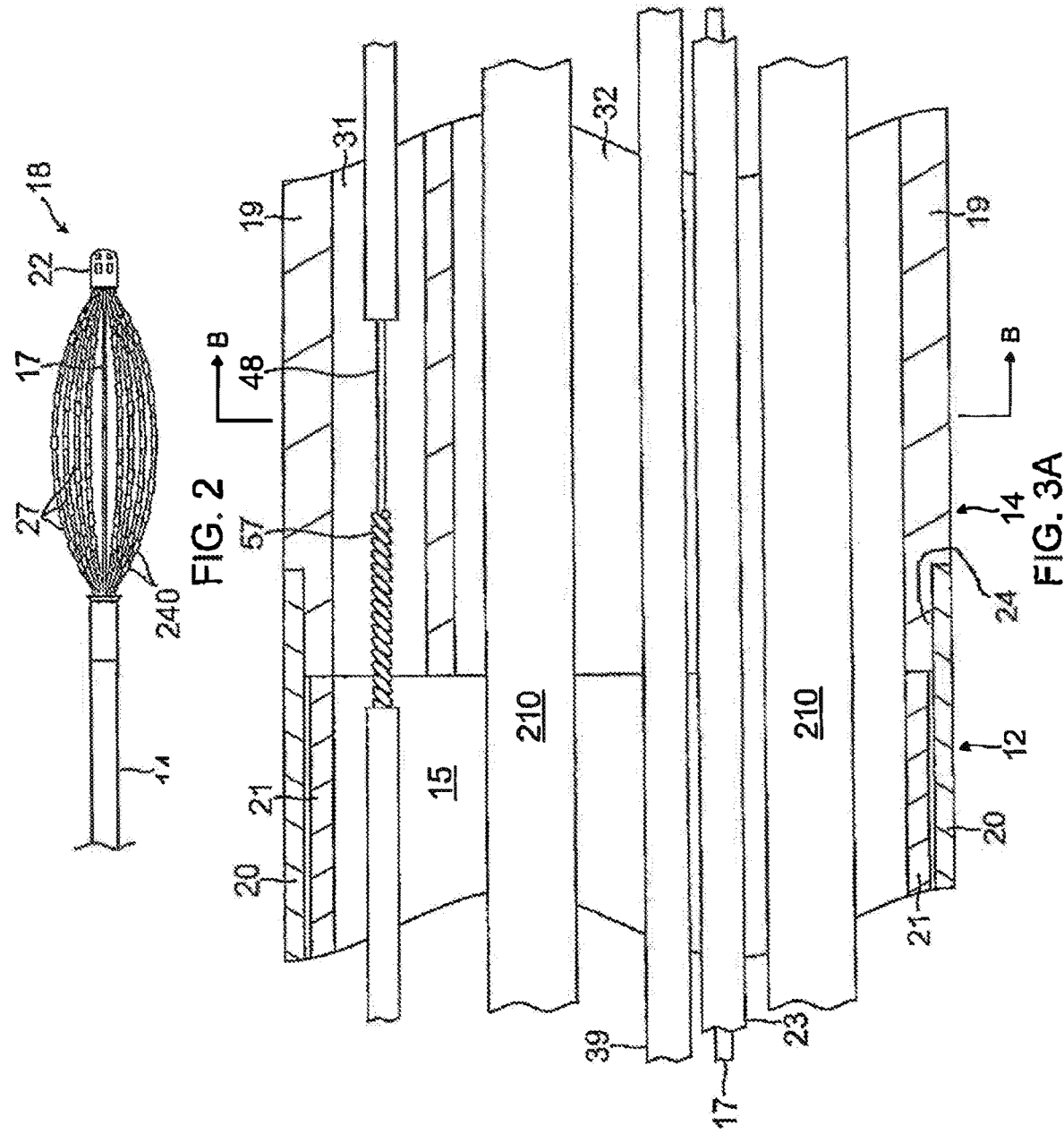

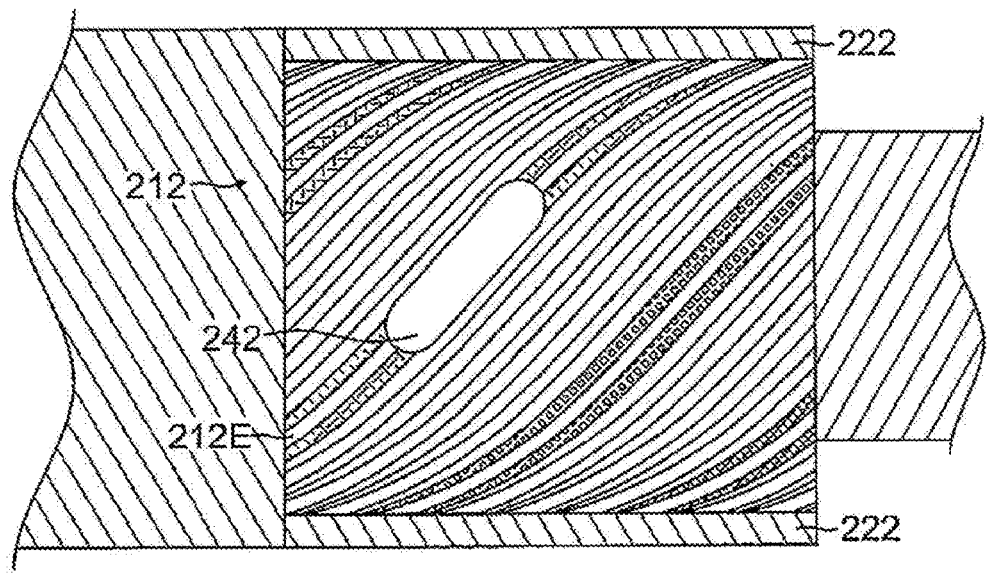
FIG. 5A
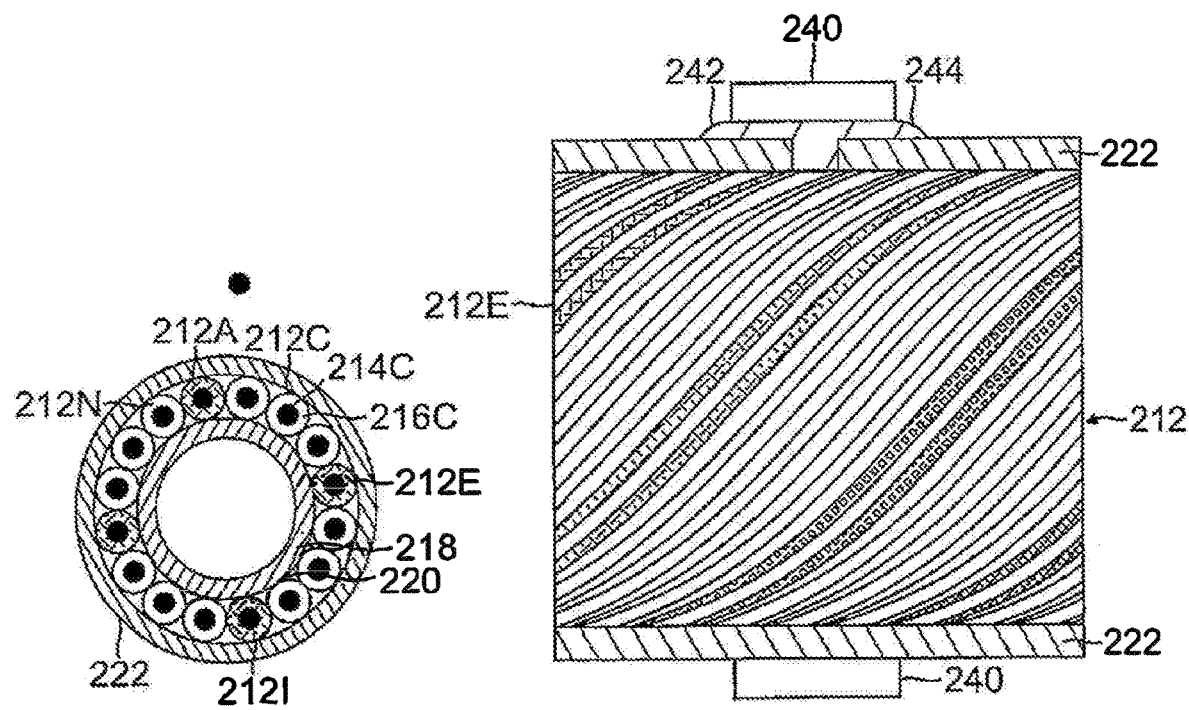
FIG. 5B
FIG. 5C

BASKET CATHETER WITH MICROELECTRODE ARRAY DISTAL TIP

CROSS-REFERENCE TO RELATED APPLICATIONS

This application is a continuation of, and claims priority to and the benefit of U.S. patent application Ser. No. 16/054,715 filed Aug. 3, 2018, now U.S. Pat. No. 10,470,714, which is a continuation of, and claims priority to and the benefit of U.S. patent application Ser. No. 15/641,182 filed Jul. 3, 2017, now U.S. Pat. No. 10,039,494, which is a continuation of, and claims priority to and the benefit of U.S. patent application Ser. No. 15/132,198 filed Apr. 18, 2016, now U.S. Pat. No. 9,693,733, which is a continuation of, and claims priority to and the benefit of U.S. patent application Ser. No. 14/526,394, filed on Oct. 28, 2014, now U.S. Pat. No. 9,314,208, the entire contents of all of which are incorporated herein by reference.

TECHNICAL FIELD

This invention relates to electrophysiologic (EP) catheters, in particular, EP catheters for mapping and/or ablation in the heart.

BACKGROUND

Electrophysiology catheters are commonly-used for mapping electrical activity in the heart. Various electrode designs are known for different purposes. In particular, catheters having basket-shaped electrode arrays are known and described, for example, in U.S. Pat. Nos. 5,772,590, 6,748,255 and 6,973,340, the entire disclosures of both of which are incorporated herein by reference.

Basket catheters typically have an elongated catheter body and a basket-shaped electrode assembly mounted at the distal end of the catheter body. The basket assembly has proximal and distal ends and comprises a plurality of spines connected at their proximal and distal ends. Each spine comprises at least one electrode. The basket assembly has an expanded arrangement wherein the spines bow radially outwardly and a collapsed arrangement wherein the spines are arranged generally along the axis of the catheter body. The catheter may further comprise a distal location sensor mounted at or near the distal end of the basket-shaped electrode assembly and a proximal location sensor mounted at or near the proximal end of the basket-shaped electrode assembly. In use, the coordinates of the distal location sensor relative to those of the proximal sensor can be determined and taken together with known information pertaining to the curvature of the spines of the basket-shaped mapping assembly to find the positions of the at least one electrode of each spine.

A basket assembly is capable of detecting in a single beat most or all of the electrical function of the left or right atrium. However, because the atria of an individual patient may vary in size and shape, it is desirable that the basket assembly be sufficiently versatile and steerable to conform to the particular atrium. A basket catheter with a deflectable basket assembly for improved maneuverability to provide better tissue contact, especially in a cavernous region of the heart, including an atrium, U.S. Publication No. 2015/0080093, the entire disclosure of which is hereby incorporated by reference.

High-density microelectrodes are also desirable for providing greater sensitivity in detecting more subtle electrical activity of heart tissue in diagnosing arrhythmias. By having a large number of electrodes often in a basket formation with spines of spaced ring electrodes, a physician can more quickly map a large area of the heart's interior geometry. Focal catheters, although lacking the resolution of a basket catheter with many electrodes, can be advantageous because their electrode location is fixed relative to the catheter distal tip.

Accordingly, it is also desirable that a basket catheter provide high-density mapping augmented with a focal diagnostic catheter tip with precisely known microelectrode locations, especially where the focal tip electrode is populated with an array of microelectrodes, in a focal catheter dimensional envelope, or even smaller, such as within a guidewire range.

SUMMARY

The present invention is directed to a basket catheter having an ultra high density microelectrode distal tip electrode comprising a non-metallic electrically insulating structure that is populated with a collection of tiny, closely spaced electrodes formed from, for example, a medical grade metal, such as palladium, platinum, gold, stainless steel and the like, and combinations thereof. The distal tip electrode may be irrigated and fitted with a location sensor. The catheter of the present invention allows for the microelectrode distal tip electrode to be deployed in a number of microelectrode configurations, and a variety of embodiments. The ultra high density microelectrode distal tip electrode may be integrated with a high density basket catheter or a standalone focal catheter, or made smaller to fit the tip of a guidewire.

The present invention is directed to a catheter having an elongated catheter body and a basket electrode assembly at the distal end of the catheter body, where the basket electrode assembly has a plurality of electrode-carrying spines and a distal end comprising a substrate body with a plurality of recessed microelectrodes. The substrate body has an outer surface and outer surfaces of the recessed microelectrodes are advantageously flush with the outer surface of the substrate body, so that the distal end presents a completely smooth and atraumatic profile.

In one embodiment, the distal end substrate body has a proximal portion with a radial outer surface and a distal portion with a domed outer surface. At least one radial microelectrode has an outer surface in conformity with the radial outer surface of the substrate body and at least one distal microelectrode has an outer surface in conformity with the domed outer surface of the substrate body. The outer surface of the substrate body is formed with indentations in which the microelectrodes are nested in a manner such that only its outer (or outer-facing) surface is exposed and even with the outer surface of the substrate body. In a more detailed embodiment, the each microelectrode has a surface area ranging between about 0.05 $mm^2$ and 0.5 $mm^2$, and preferably about 0.15 $mm^2$. The substrate body may carry a plurality of microelectrodes ranging between about two and 20, preferably between about six and 16. Moreover, lead wires connected to the microelectrodes are passed through radial and distal passages formed in the substrate body.

The present invention is also directed to a focal catheter having an elongated catheter body and a distal tip with a substrate body and a plurality of recessed microelectrodes, whose outer surface is flush with the outer surface of the substrate body. The distal tip of the focal catheter has all the aforementioned structural advantages for greater mapping resolution and greater location precision.

BRIEF DESCRIPTION OF THE DRAWINGS

These and other features and advantages of the present invention will be better understood by reference to the following detailed description when considered in conjunction with the accompanying drawings wherein:

FIG. 2 is a detailed view of the basket electrode assembly of FIG. 1, in a collapsed configuration.

FIG. 3A is a side cross-sectional view of the catheter of the present invention, including a junction between a catheter body and a deflection section, along a diameter.

FIG. 5A is a top view of a cabling for use with the present invention, according to one embodiment, with part(s) broken away.

FIG. 5B is an end cross-sectional view of the cabling of FIG. 5A.

FIG. 5C is a side view of the cabling of FIG. 5A, with part(s) broken away.

DETAILED DESCRIPTION

Figure 1:
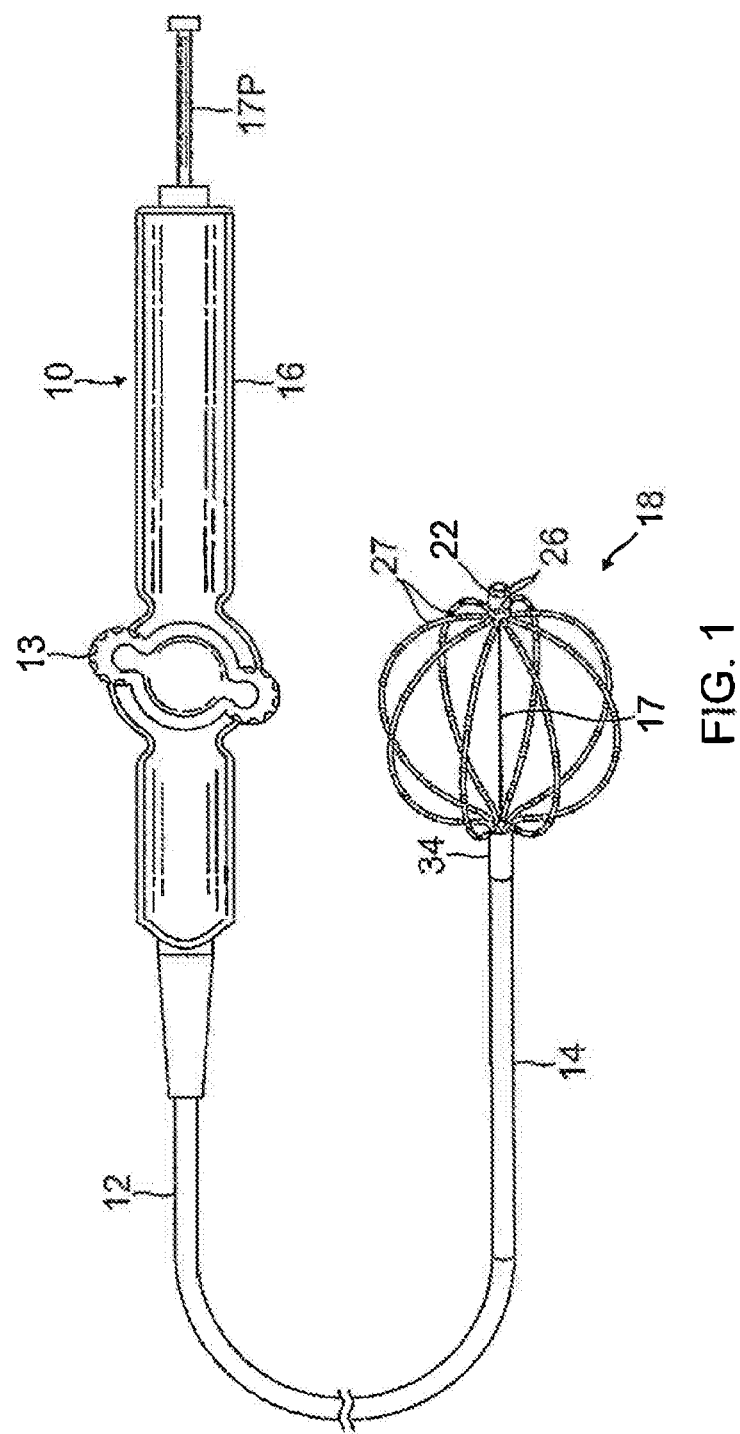
FIG. 1 is a top plan view of a catheter of the present invention, according to one embodiment, with a basket electrode assembly in an expanded, deployed configuration.

The invention is directed to a catheter 10 having a basket-shaped, high density electrode assembly 18 for large-area mapping, with an integrated distal tip 22 providing an array of ultra high density microelectrodes for acute focal mapping. As shown in FIG. 1, the catheter 10 comprises an elongated catheter body 12 having proximal and distal ends, a control handle 16 at the proximal end of the catheter body, an intermediate deflection section 14 distal of the catheter body 12, and the basket-shaped electrode assembly 18 at the distal end of the deflection section 14. The basket-shaped electrode assembly (or "basket assembly") 18 has a plurality of spines 27 whose proximal ends and distal ends surround an elongated expander 17 that is afforded longitudinal movement relative to the catheter for adjusting the shape of the basket assembly between an expanded configuration (FIG. 1) and a collapsed configuration (FIG. 2). Mounted on the distal end of the basket assembly 18 is the distal tip 22 having a plurality of surface-embedded microelectrodes 26 whose outer surface is generally flush with the outer surface of the substrate body to present a generally smooth, atraumatic distal tip profile.

With reference to FIG. 3A, the catheter body 12 comprises an elongated tubular construction having a single, axial or central lumen 15, but can optionally have multiple lumens if desired. The catheter body 12 is flexible, i.e., bendable, but substantially non-compressible along its length. The catheter body 12 can be of any suitable construction and made of any suitable material. One construction comprises an outer wall 20 made of polyurethane or PEBAX® (polyether block amide). The outer wall 20 comprises an imbedded braided mesh of stainless steel or the like to increase torsional stiffness of the catheter body 12 so that, when the control handle 16 is rotated, the distal end of the catheter body will rotate in a corresponding manner.

The outer diameter of the catheter body 12 is not critical, but may be no more than about 8 french, more preferably 7 french. Likewise the thickness of the outer wall is not critical, but is preferably thin enough so that the central lumen 15 can accommodate a puller wire, lead wires, sensor cable and any other wires, cables or tubes. If desired, the inner surface of the outer wall is lined with a stiffening tube 21 to provide improved torsional stability. An example of a catheter body construction suitable for use in connection with the present invention is described and depicted in U.S. Pat. No. 6,064,905, the entire disclosure of which is incorporated herein by reference.

Figure 3B:
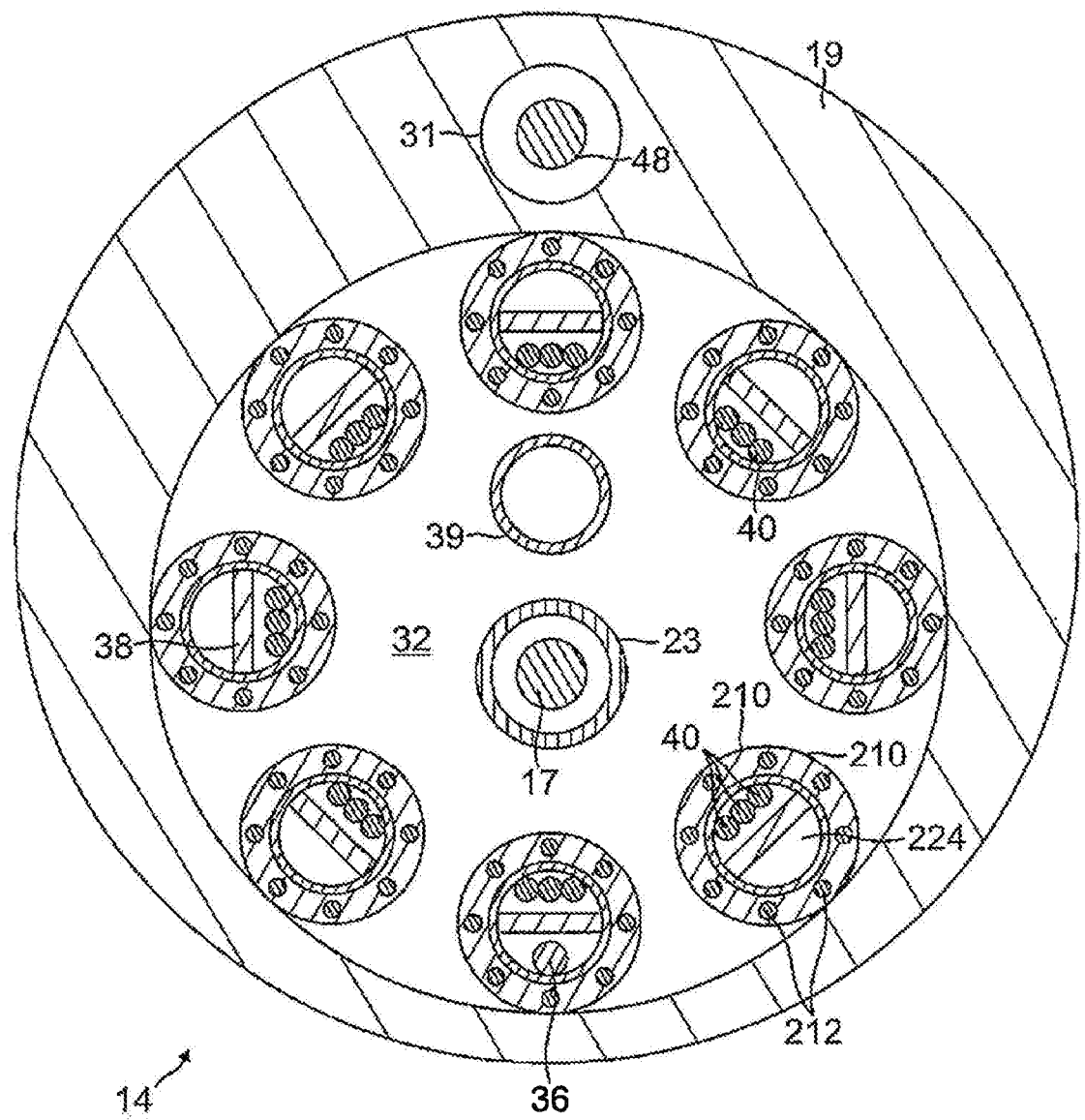
FIG. 3B is an end cross-sectional view of the deflection section of FIG. 3A, taken along line B-B.

Distal of the catheter body 12 is the intermediate deflection section 14 which comprises a multi-lumened tubing 19, with, for example, at least two off axis lumens 31 and 32, as shown in FIGS. 3A and 3B. The multi-lumened tubing 19 is made of a suitable non-toxic material that is preferably more flexible than the catheter body 12. In one embodiment, the material for the tubing 19 is braided polyurethane or thermoplastic elastomer (TPE), for example, polyether block amide (PEBAX®), with an imbedded mesh of braided high-strength steel, stainless steel or the like. The outer diameter of the deflection section 14 is no greater than that of the catheter body 12. In one embodiment, the outer diameter is no greater than about 8 french, more preferably about 7 french. Larger or smaller embodiments are possible, as determined by the number of spines in the basket, if applicable. The size of the lumens is not critical, so long as the lumens can accommodate the components extending therethrough.

A means for attaching the catheter body 12 to the deflection section 14 is illustrated in FIG. 3A. The proximal end of the deflection section 14 comprises an outer circumferential notch 24 that receives the inner surface of the outer wall 20 of the catheter body 12. The deflection section 14 and catheter body 12 are attached by adhesive (e.g. polyurethane glue) or the like. Before the deflection section 14 and catheter body 12 are attached, however, the stiffening tube 21 is inserted into the catheter body 12. The distal end of the stiffening tube 21 is fixedly attached near the distal end of the catheter body 12 by forming a glue joint (not shown) with polyurethane glue or the like. Preferably, a small distance, e.g., about 3 mm, is provided between the distal end of the catheter body 12 and the distal end of the stiffening tube 21 to permit room for the catheter body 12 to receive the notch 24 of the deflection section 14. A force is applied to the proximal end of the stiffening tube 21, and, while the stiffening tube 21 is under compression, a first glue joint (not shown) is made between the stiffening tube 21 and the outer wall 20 by a fast drying glue, e.g. Super Glue® Thereafter, a second glue joint (not shown) is formed between the proximal ends of the stiffening tube 21 and outer wall 20 using a slower drying but stronger glue, e.g. polyurethane.

Figure 4A:
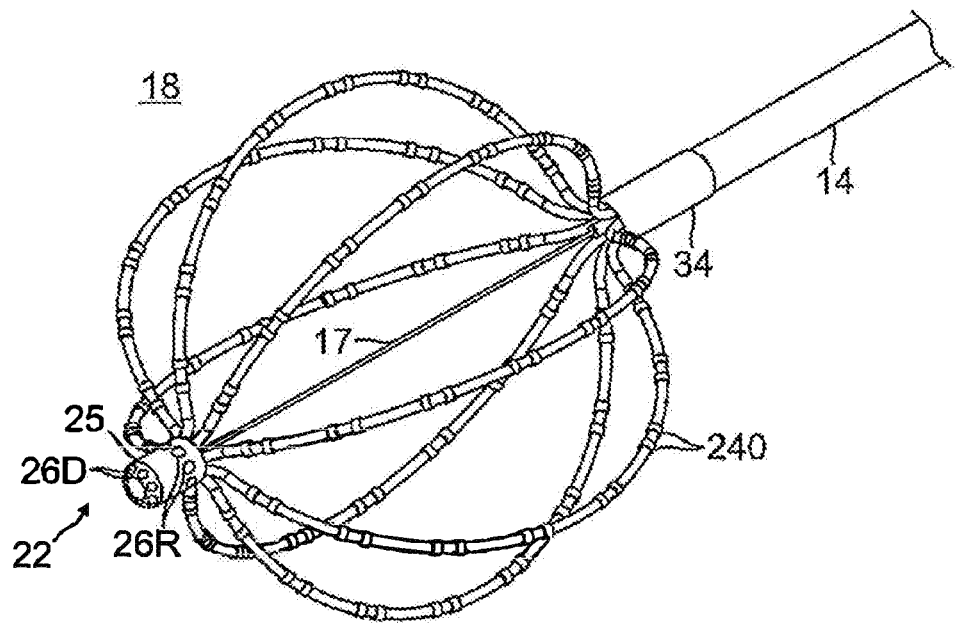
FIG. 4A is a detailed view of the basket electrode assembly of FIG. 1, in an expanded, deployed configuration.

The basket-shaped electrode assembly 18 is mounted to the distal end of the catheter body 12. As shown in FIGS. 1 and 4A, the basket-shaped electrode assembly 18 comprises a plurality of electrode-carrying spines 27 or arms (e.g., between about five to ten, and preferably about eight) mounted, generally evenly-spaced in about 360 radial degrees around the expander 17 so that the expander forms the center longitudinal axis of the electrode assembly. Each of the spines 27 is attached, directly or indirectly, at its distal end to the distal end of the expander 17. As actuated by longitudinal movement of the expander 17 relative to the catheter, the basket assembly 18 is adapted to assume an elongated and collapsed configuration with the expander 17 extended distally (FIG. 2) and a deployed and radially expanded configuration with the expander drawn proximally (FIG. 1). The expander 17 comprises a material sufficiently rigid to achieve this function. In an embodiment, the expander 17 is a wire or tensile member, and a guide tube 23 is provided to surround, protect and guide the expander 17 through the control handle 16, the catheter body 12 and the deflection section 14. The guide tube 23 is made of any suitable material, including polyimide.

In one embodiment, each spine 27 of the basket assembly 18 comprises a cabling 210 with build-in or embedded lead wires 212, as shown in FIGS. 5A, 5B and 5C. The cabling has a core 218, and a plurality of generally similar wires 212 covered by an insulating layer 216 that enables each wire to be formed and to function as a conductor 214. The core 218 provides a lumen 224 in which can pass other components such as additional lead wire(s), cables, tubing and/or a support structure to shape the cabling as desired.

In the following description, generally similar components associated with cabling 210 are referred to generically by their identifying component numeral, and are differentiated from each other, as necessary, by appending a letter A, B, . . . to the numeral. Thus, wire 212C is formed as conductor 214C covered by insulating layer 216C. While embodiments of the cabling may be implemented with substantially any plurality of wires 212 in the cabling, for clarity and simplicity in the following description cabling 210 is assumed to comprise N wires 212A, 212B, 212C, . . . 212N, where N equals at least the number of ring electrodes on each respective spine of the basket assembly 18. For purposes of illustration, insulating layers 216 of wires 212 have been drawn as having approximately the same dimensions as conductors 214. In practice, the insulating layer is typically approximately one-tenth the diameter of the wire.

The wires 212 are formed over an internal core 218, which is typically shaped as a cylindrical tube, and core 218 is also referred to herein as tube 218. The core material is typically selected to be a thermoplastic elastomer such as a polyether block amid (PEBA) or PEBAX®. Wires 212 are formed on an outer surface 220 of the core 218 by coiling the wires around the tube 218. In coiling wires 212 on the surface 220, the wires are arranged so that they contact each other in a "close-packed" configuration. Thus, in the case that core 218 is cylindrical, each wire 212 on the outer surface is in the form of a helical coil. In the case of the tube 218 being cylindrical, the close packed arrangement of the helical coils of wires 212 means that the wires are configured in a multi-start thread configuration. Thus, in the case of the N wires 212 assumed herein, wires 212 are arranged in an N-start thread configuration around cylindrical tube 218.

In contrast to a braid, all helical coils of wires 212 herein have the same handedness (direction of coiling). Moreover, wires in braids surrounding a cylinder are interleaved, so are not in the form of helices. Because of the non-helical nature of the wires in braids, even braid wires with the same handedness do not have a threaded form, let alone a multi-start thread configuration. Furthermore, because of the lack of interleaving in arrangements of wires in embodiments of the cabling, the overall diameter of the cabling produced is less than that of cabling using a braid, and the reduced diameter is particularly beneficial when the cabling is used for a catheter.

Once wires 212 have been formed in the multi-start thread configuration described above, the wires are covered with a protective sheath 222. The protective sheath material is typically selected to be a thermoplastic elastomer such as PEBA, for example, 55D PEBAX without additives so that it is transparent. In that regard, insulating layer of at least one of wires 212 is colored differently from the colors of the remaining wires as an aid in identifying and distinguishing the different wires.

The process of coiling wires 212 around the core 218, and then covering the wires by the sheath 222 essentially embeds the wires within a wall of cabling 210, the wall comprising the core and the sheath. Embedding the wires within a wall means that the wires are not subject to mechanical damage when the cabling is used to form a catheter. Mechanical damage is prevalent for small wires, such as 48AWG wires, if the wires are left loose during assembly of a catheter.

In use as a catheter, an approximately cylindrical volume or lumen 224 enclosed by the core 218, that is afforded by embedding smaller wires (such as the 48 AWG wires) in the wall, allows at least a portion of the lumen 224 to be used for other components. It is understood that the plurality of wires 212 shown in the drawings is representative only and that a suitable cabling provides at least a plurality of wires equal to or greater than the plurality of ring electrodes mounted on each cabling or spine of the basket assembly. Cabling suitable for use with the present invention is described in U.S. Publication Nos. 2014/0309512 and 2014/0305699, the entire disclosures of which are incorporated herein by reference. Each cabling 210 (with embedded lead wires 212) extends from the control handle 16, through the lumen 15 of the catheter body 12, and the larger lumen 32 of the tubing 19 of the deflection section 14, as shown in FIG. 3A.

Figure 6A:
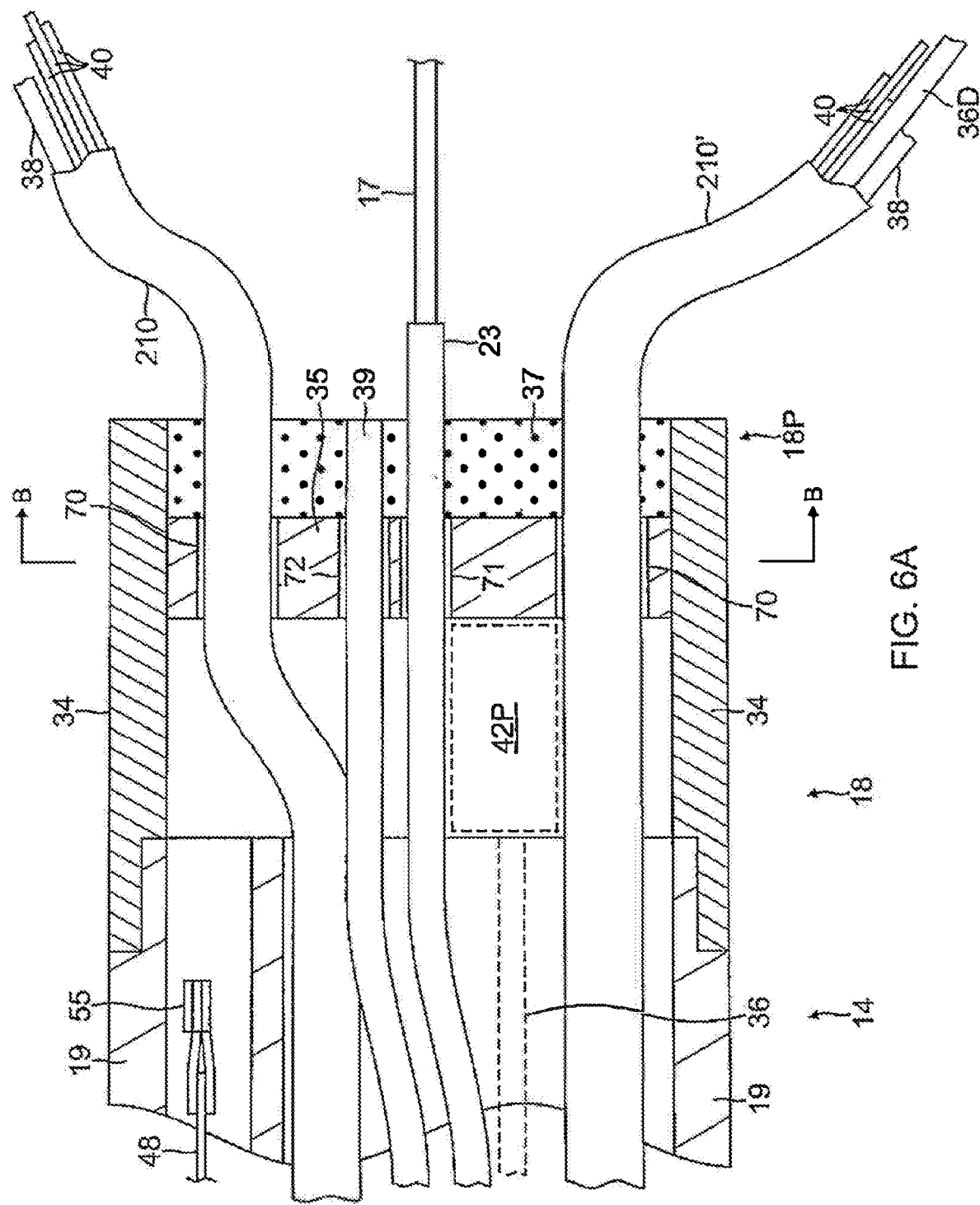
FIG. 6A is a side cross-sectional view of a proximal junction of the basket electrode assembly, according to one embodiment.
Figure 6B:
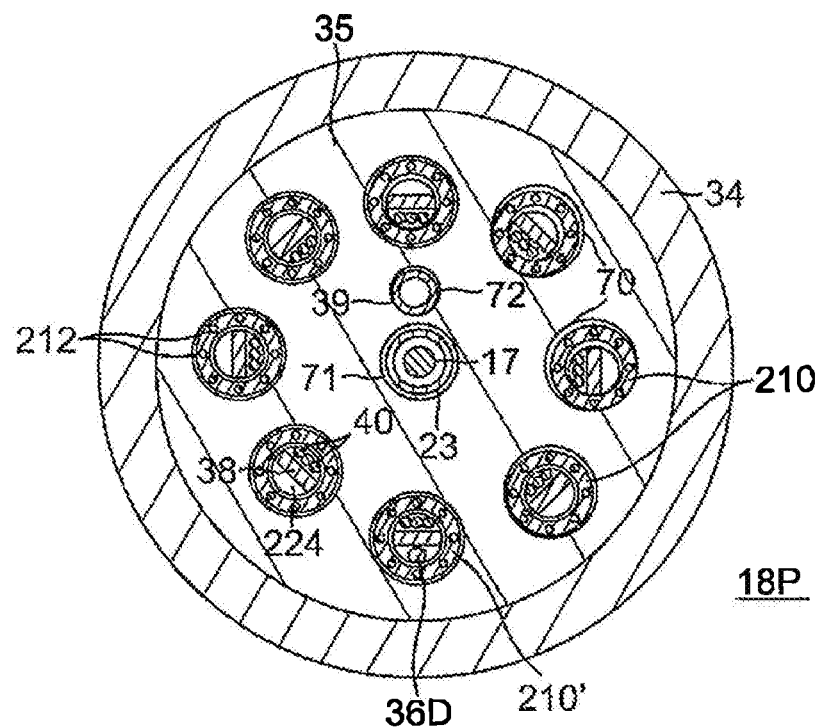
FIG. 6B is an end cross-section view of the proximal junction of FIG. 6A, taken along line B-B.

With reference to FIGS. 6A and 6B, at the proximal end of the basket assembly 18, the cabling 210 (serving as the spines 27 of the basket assembly 18, and used interchangeably herein) extend through a proximal junction 18P that includes an outer tubing 34 that extends a short distance from the distal end of the tubing 19 of the deflection section 14. The outer tubing 34 may be made of any suitable material, for example, PEEK (polyetheretherketone).

In the lumen of the outer tubing 34, a proximal alignment disc 35 formed with a plurality of through-holes is provided to receive and position the cabling 210 and the guide tube 23 of the expander 17 in the outer tubing 34. The proximal disc 35 is made of any suitable material, including metal or plastic. In the embodiment of FIGS. 6A and 6B, the proximal disc 35 has an on-axis through-hole 71 for the guide tube 23, and a plurality of off-axis through-holes 70 around a peripheral region of the disc, with each through-hole guiding a respective cabling 210 (only two of which are shown in FIG. 6A for clarity). For example, with eight cabling 210, the through-holes 70 are situated at about 45 radial degrees around the peripheral region. Where irrigation is desired, the disc 35 includes another off-axis through-hole 72 which receives a distal end of an irrigation tubing 39 from which fluid passing through the tubing 39 exits the catheter. Distal of the disc 35, the lumen of the outer tubing 34 is filled and sealed with a suitable glue 37, for example, epoxy.

The cabling 210 and the expander 17 extend distally from the proximal junction 18P to form the basket assembly 18. Each cabling has a predetermined shape flexibly set by a shape memory member 38 that extends through the lumen 224 in the core 218. As shown in FIG. 3B, selected or all of the lumens 224 of the cores 218 also carry additional lead wires 40 for the array of microelectrodes 26 on the distal tip 22. Selected lumens 224 may also carry cable(s) 36 for electromagnetic location sensor(s) carried in the distal tip 22.

In forming the basket shape, the shape memory members 38 in the cabling 210 diverge from the proximal junction 18P and bow outwardly from the expander 17, and converge at their distal ends at the distal tip 22, as shown in FIG. 4A. The shape memory member 38, e.g., a Nitinol shape member or wire, is configured to flexibly provide the shape of the basket-assembly, as known in the art. In one embodiment, the shape memory member 38 of each cabling 210 has a proximal end located near the proximal end of the deflection section 14, and a distal end located in the distal tip 22, although it is understood that the proximal end may be located anywhere proximally of the proximal end of the deflection section 14 along the length of the cabling 210, as desired or appropriate.

As understood by one skilled in the art, the number of spines 27 or cabling 210 of the basket assembly 18 can vary as desired depending on the particular application, so that the basket assembly 18 has at least two spines, preferably at least three spines, and as many as eight or more spines. As used herein, the term "basket-shaped" in describing the electrode assembly 18 is not limited to the depicted configuration, but can include other designs, such as spherical or egg-shaped designs, that include a plurality of expandable arms connected, directly or indirectly, at their proximal and distal ends.

Each spine 27 or cabling 210 carries a plurality of ring electrodes 240, which may be configured as monopolar or bipolar, as known in the art. FIGS. 5A and 5B are schematic diagrams illustrating attachment of a ring electrode 240 to cabling 210, according to an embodiment. FIG. 5A is a schematic top view of the cabling and FIG. 5B is a schematic side view of the cabling; in both views portions of sheath 222 have been cut away to expose wires 212 of the cabling 210, as well as to illustrate the attachment of a ring electrode 240 to the cabling 210. FIG. 5A illustrates cabling 210 before attachment of ring electrode 240, and FIG. 5B illustrates the cabling after the ring electrode has been attached. Ring electrode has dimensions enabling it to be slid over sheath 222.

Initially a location for attaching a ring electrode 240 is selected by visually finding a colored wire, such as wire 212E. The visual determination is possible since sheath 222 is transparent. Once the location has been selected, a section of sheath 222 above the wire and a corresponding section of insulating layer 216E are removed to provide a passage 242 to conductor 214E. In a disclosed embodiment, conductive cement 244 is fed into the passage, ring electrode 240 is slid to contact the cement, and the electrode is then crimped in place. Alternatively, the ring electrode 240 may be attached to a specific wire by pulling the wire through sheath 222, and resistance welding or soldering the ring electrode to the wire.

Figure 4B:
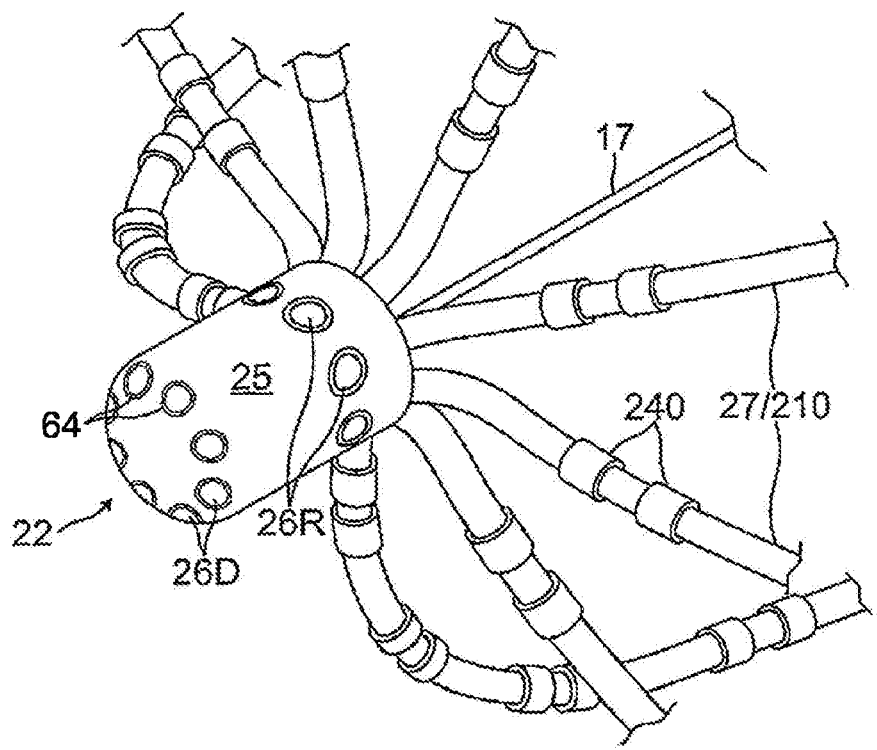
FIG. 4B is a detailed view of a distal end of the basket electrode assembly of FIG. 4A.
Figure 7B:
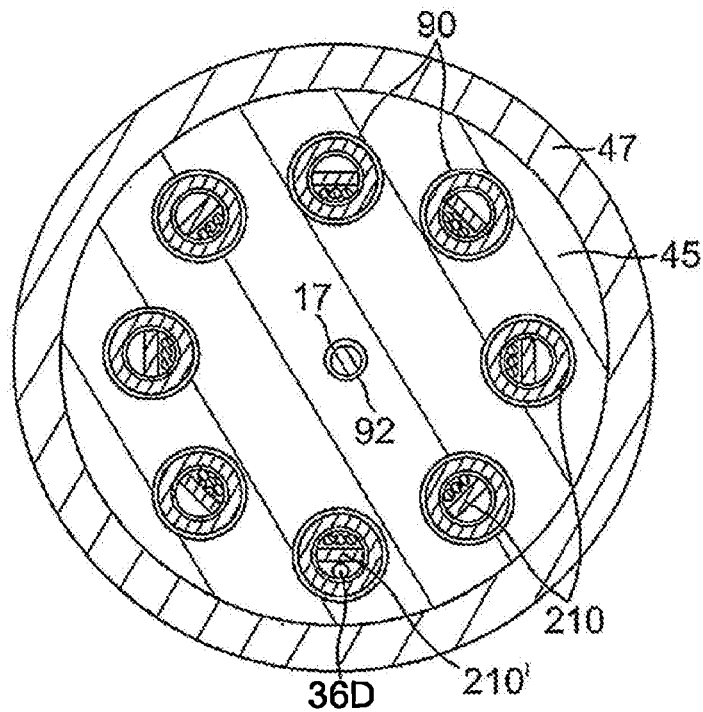
FIG. 7B is an end cross-sectional view of the distal tip of FIG. 7A, taken along line B-B.
Figure 7A:
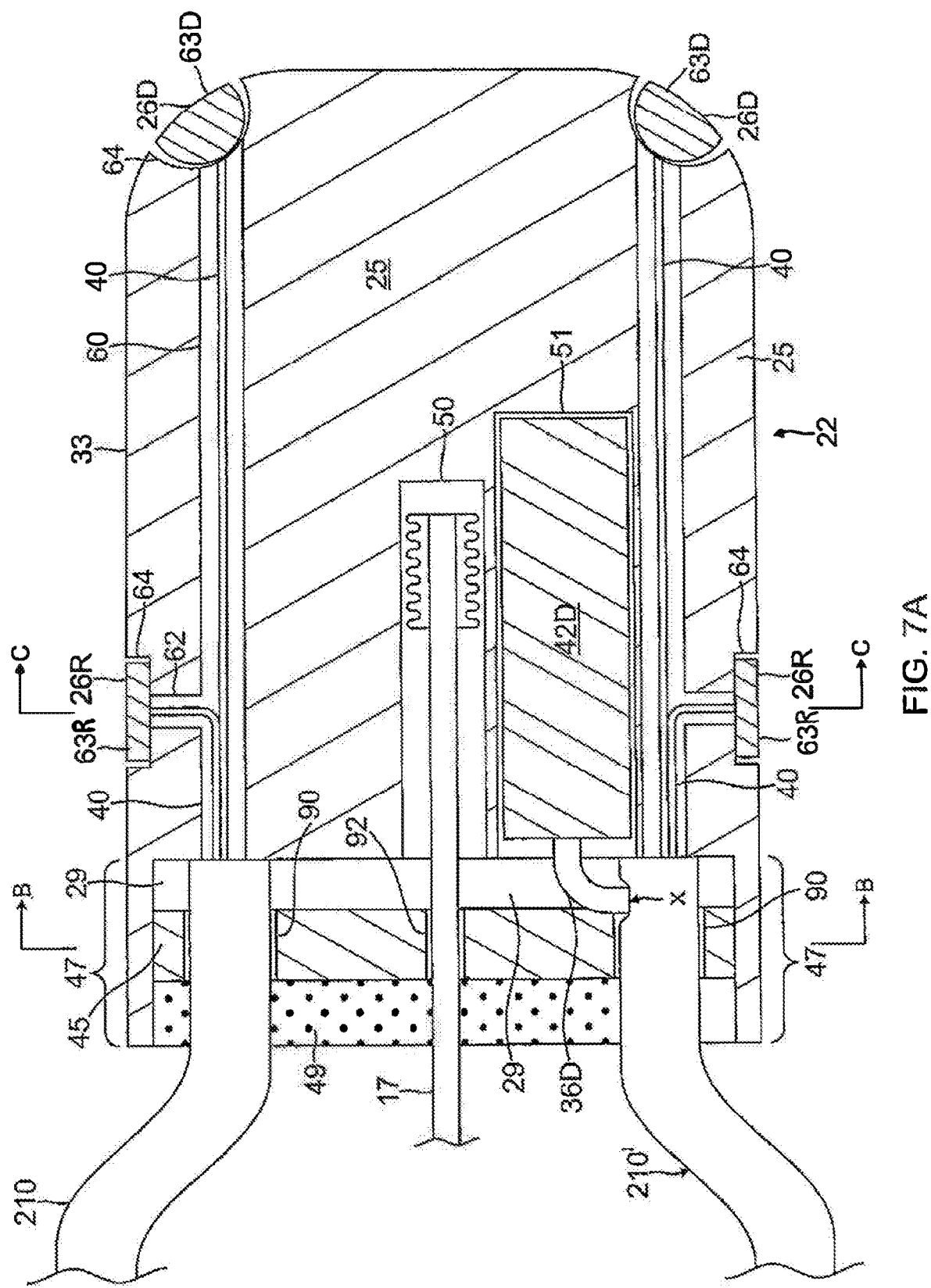
FIG. 7A is a side cross-sectional view of a distal tip, in accordance with one embodiment.

With reference to FIGS. 4B, 7A and 7B, at the distal end of the basket assembly 18, the distal ends of the cabling 210 converge around the distal end of the expander 17 in the distal tip 22. The distal tip 22 has a generally solid, elongated, nonmetallic, electrically-insulating substrate body 25 with a generally cylindrical shape (with a two-dimensional curvature in the X/Y direction and a linear length in the Z direction), and a domed distal end (with a three-dimensional curvature in the X/Y/Z direction). The body has a trepanned proximal face 47 forming a cored-out proximal region 29 in which the distal ends of the cabling 210 and the expander 17 are received, anchored and sealed by glue 49, for example, epoxy. A first, on-axis blind hole 50 extends distally from the cored-out proximal region to receive a crimped distal tip of the expander 17. A second, off axis blind hole 52 extends distally from the cored-out proximal region 29 to receive at least a portion of the electromagnetic location sensor 42.

The distal ends of the cabling 210 in the cored-out proximal region 29 are positioned by a distal alignment disc 45. The disc 45 has a plurality of through-holes to receive the cabling 210 and the expander 17 in the outer tubing 34. The disc 45 is made of any suitable material, including metal or plastic. In the embodiment of FIGS. 7A and 7B, the distal disc 45 has an on-axis through-hole 92 for the expander 17, and a plurality of off-axis through-holes 90 around a peripheral region of the disc, with each through-hole guiding the distal end of a respective cabling 210 (only two of which are shown in FIG. 7A for clarity). For example, with eight cabling 210, the through-holes 90 are situated at about 45 radial degrees around the peripheral region. Proximal of the disc 45, the cored-out proximal region 29 is filled and sealed with a suitable glue 49, for example, epoxy.

Also formed in the body 25 of the distal tip 22 are axial passages 60 and radial passages 62, as shown in FIG. 7A, providing communication between the cored-out proximal region 29 and indentations 64 formed on outer surface 33 of the body 25 where the microelectrodes 26 are located. With respective pairs of the cabling 210 and axial passages 60 axially aligned with each other in the tip 22, the additional lead wires 40 that pass through the lumen 224 of the core 218 of the cabling 210 extend through the axial and radial passages 60 and 62 for connection to the respective microelectrodes and/or temperature sensing in the distal tip 22. Radial microelectrodes 26R are located on radial outer surface of the body 25. Distal microelectrodes 26D are located on distal outer surface of the body 25. It is understood that the plurality of wires 40 shown in the drawings is representative only and that the plurality of wires is equal to or greater than the plurality of microelectrodes carried on the distal tip 22. Also passing through the lumen 224 of the core 218 of one predetermined cabling 210' is the cable 36D for the distal EM location sensor 42D. A portion of the wall of the cabling 210' is removed at X so as to accommodate the cable 36D extending from a distal EM location sensor 42D.

Figure 7C:
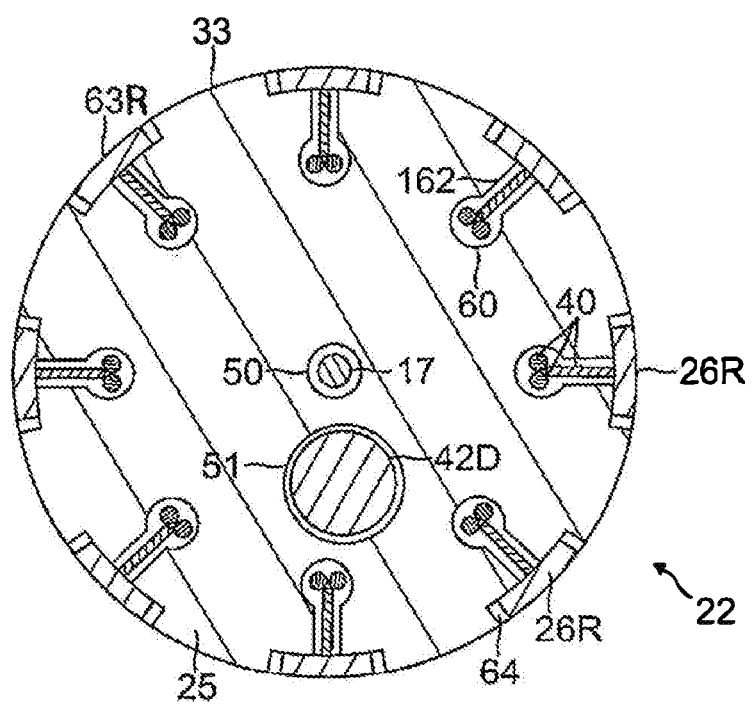
FIG. 7C is an end cross-sectional view of the distal tip of FIG. 7A, taken along line C-C.

In accordance with a feature of the present invention, the indentations 64 are shaped and sized in correspondence with the shape and size of the microelectrode 26 which has a body that is fully received in a respective indentation 64 such that only an outer or outer-facing surface 63 of the microelectrode is exposed and generally even and flush with the outer surface 33 of the body 25 of the distal tip 22, as shown in FIGS. 7A and 7C. The indentations 64 allow the microelectrodes 26 to be recessed in the body 25 to provide a smooth and atraumatic profile which minimizes the risk of the microelectrodes snagging, scratching or otherwise damaging tissue in contact with the distal tip 22. Each indentation minimizes, if not prevents, contact between tissue and a microelectrode except by the outer surface 63 of the microelectrode. The indentation limits tissue contact by any side surface or inner surface of a microelectrode by surrounding the microelectrode except for the outer surface.

Moreover, the outer surface 63 of the microelectrode 26 has the same contour as the surrounding outer surface 33 of the substrate body 25. For example, the distal microelectrodes 26D have three-dimensionally curved outer surfaces 63D that conform with the three-dimensionally curved outer surface 33 of the substrate body 25 at its distal end, and the radial microelectrodes 26R have two-dimensionally curved outer surfaces 63R that conform with the two-dimensionally curved outer surfaces 33 of the substrate body 25. With a generally smooth profile, the tip 22 can be pivoted about its distal end in a circular motion where its longitudinal axis traces a cone C to improve electrode contact with minimum risk of damage to tissue, especially in a cavernous region, such as an atrium.

Each microelectrode 26 has a surface area ranging between about 0.05 mm$^2$ and 0.5 mm$^2$, and preferably 0.15 mm$^2$. Thus, the distal tip 22 comprises a plurality of tiny, closely spaced electrodes that may be formed from any suitable material, including medical-grade metal, for example, palladium, platinum, gold, stainless steel and the like, and combinations thereof. With a large number of microelectrodes 26, the tip 22 advantageously provides focal diagnostic capabilities with precisely known microelectrode locations by means of their fixed location relative to the tip body 25, whereas the basket assembly 18 with its large number of ring electrodes 240 on the spines 27 allows the physician to more quickly cover a large area of internal geometry of a cavernous region, such as the heart.

Each of the ring electrodes 240 on the spines 27 and each of the microelectrodes 26 is electrically connected via the lead wires 212 and 40, respectively, to an appropriate mapping system and/or source of ablation energy remote from the catheter by means of a multi-pin connector (not shown) at the proximal end of the control handle 16. The cabling 210 with embedded electrode lead wires 212 in its wall and additional lead wires 40 and EM sensor cable 36 in its lumen 224 pass from the control handle 16 and through the central lumen 15 of the catheter body 12 and the lumen 32 of the deflection section 14 and extends through the basket assembly 18 as the spines where lead wires 212 are connected to the ring electrodes, the lead wires 40 are connected to the microelectrodes 26 on the distal tip 22 and the cable 36 to the EM sensor in the distal tip 22. By combining the basket assembly 18 with a microelectrode distal tip 22, the catheter is adapted for both large area mapping and acute focal mapping.

The expander 17 has a suitable length that extends the entire length of the catheter. The expander includes a proximal end 17P (FIG. 1) that is exposed proximally of the control handle 16, a main portion that extends through the control handle 16, the central lumen 15 of the catheter body 12, and the lumen 32 of the deflection section 14, and an exposed distal portion extending through the basket assembly 18 and into the distal tip 22. The guide tube 23 extends through the control handle 16, the central lumen 15 of the catheter body, and the lumen 32 of the deflection section 14 and has distal end that extends a short distance distal of the distal end of the outer tubing 34 of the proximal junction 18P of the basket assembly 18. A user manipulates the proximal end 17P by advancing or withdrawing the expander 17 longitudinally relative to the control handle 16 and the catheter so that it can move the distal ends of the spines 27 proximally or distally relative to the catheter to radially expand and contract, respectively, the assembly 18.

As shown in FIGS. 3A and 3B, a puller wire 48 for uni-directional deflection of the deflection section 14 extends from the control handle 16 where its proximal end is anchored and responsive to a deflection knob 13 on the control handle 16, and through the central lumen 15 of the catheter body 12 and the lumen 31 of the deflection section 14. As shown in FIG. 6A, a distal end of the puller wire 48 is anchored near the distal end of the deflection section 14 by a T-bar 55 as known in the art. Along the length of the lumen 15 of the catheter body 12, the puller wire is surrounded by a compression coil 57, as shown in FIG. 3A. The compression coil has a proximal end at or near a junction between the control handle 16 and the catheter body 12, and a distal end at or near the distal end of the catheter body 12. Accordingly, when the puller wire 48 is drawn proximally by manipulation of the deflection knob 13 (FIG. 1) on the control handle 16, the compression coil 57 stops compression along its length so that the puller wire 48 deflects the deflection section 14 distal of the catheter body 12. The catheter may include a second puller wire for bi-directional deflection, as known in the art.

A distal electromagnetic location sensor 42D is connected to sensor cable 36D that extends through the lumen 224 of selected cabling 210' (FIG. 3B) which extends from the catheter body 12 and control handle 16 and out the proximal end of the control handle 16 (FIG. 1) within an umbilical cord (not shown) to a sensor control module (not shown) that houses a circuit board (not shown). Alternatively, the circuit board can be housed within the control handle 16, for example, as described in U.S. Pat. No. 6,024,739, the disclosure of which is incorporated herein by reference. The sensor cable 36D comprises multiple wires encased within a plastic covered sheath. In the sensor control module, the wires of the sensor cable are connected to the circuit board. The circuit board amplifies the signal received from the corresponding location sensor and transmits it to a computer in a form understandable by the computer by means of the sensor connector at the proximal end of the sensor control module. Also, because the catheter is designed for single use only, the circuit board may contain an EPROM chip that shuts down the circuit board approximately twenty-four hours after the catheter has been used. This prevents the catheter, or at least the location sensor, from being used twice.

In one embodiment, the location sensor 42D comprises a magnetic-field-responsive coil, as described in U.S. Pat. No. 5,391,199, or a plurality of such coils, as described in International Publication WO 96/05768. The plurality of coils enables six-dimensional position and orientation coordinates to be determined. Alternatively, any suitable location sensor known in the art may be used, such as electrical, magnetic or acoustic sensors. Suitable location sensors for use with the present invention are also described, for example, in U.S. Pat. Nos. 5,558,091, 5,443,489, 5,480,422, 5,546,951, and 5,568,809, and International Publication Nos. WO 95/02995, WO 97/24983, and WO 98/29033, the disclosures of which are incorporated herein by reference. In one embodiment, an electromagnetic mapping sensor has a length of from about 3 mm to about 7 mm, preferably about 4 mm.

A proximal EM location sensor 42P may be provided at the proximal end of the basket assembly 18, as shown in broken lines in FIG. 6A. The sensor 42P is housed in the outer tubing 34 and a cable 36P, also shown in broken lines in FIG. 6A, for the proximal location sensor 42P may extend through the central lumen 15 of the catheter body 12, and the lumen 32 of the deflection section 14. With a second location sensor, the coordinates of the distal sensor 42D, relative to those of the proximal sensor 42P, are determined and taken together with other known information pertaining to the curvature of the spines 27 of the basket-shaped mapping assembly 18. This information is used to find the positions of the ring electrodes 240 mounted on the spines 26.

As would be recognized by one skilled in the art, other arrangements for constructing the proximal and distal junctions and for mounting the location sensors could also be used in accordance with the invention.

Figure 8:
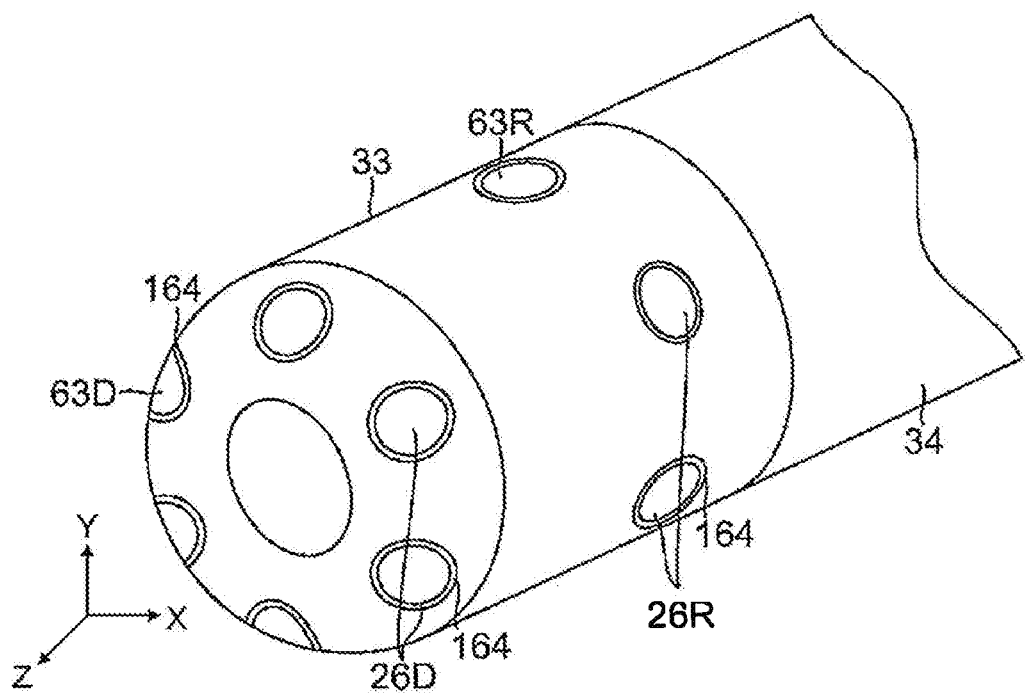
FIG. 8 is a detailed perspective view of a distal tip of a focal catheter, in accordance with one embodiment.
Figure 9:
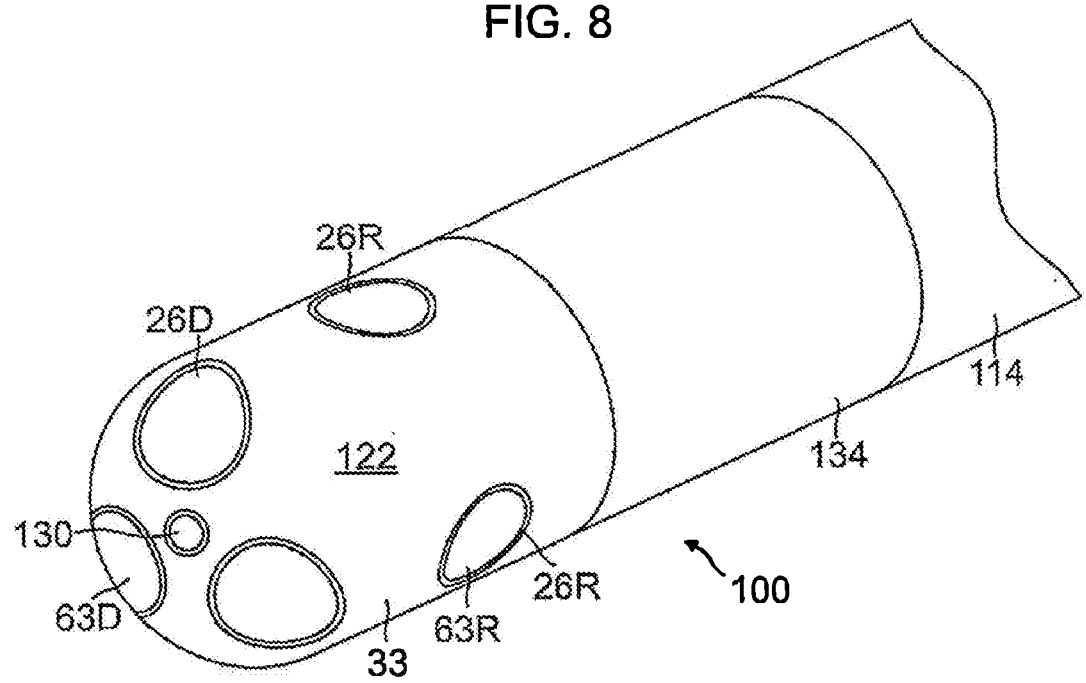
FIG. 9 is a detailed perspective view of a distal tip of a focal catheter with a guidewire passage, in accordance with one embodiment.
Figure 10:
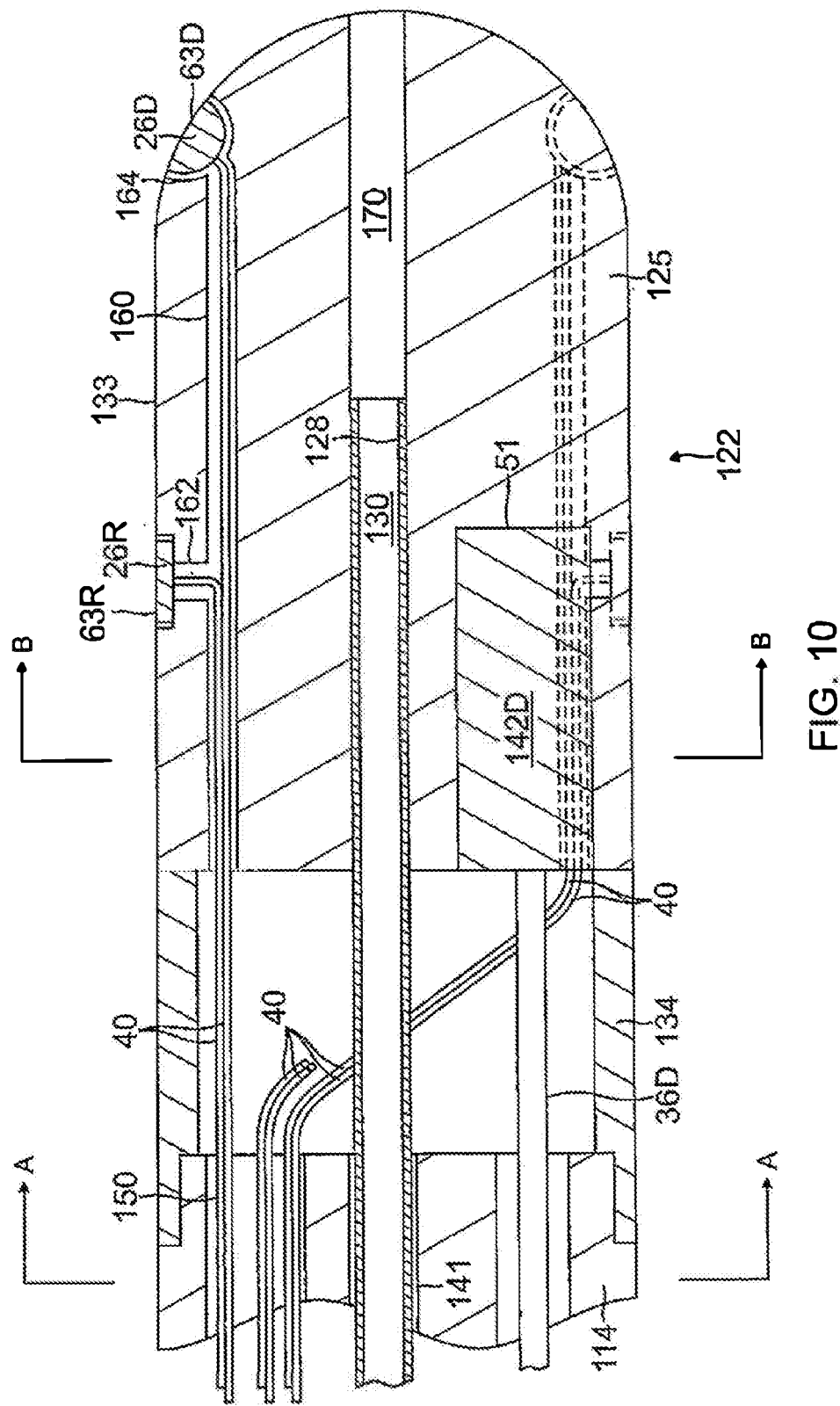
FIG. 10 is a side cross-sectional view of the distal tip of FIG. 9.
Figure 10A:
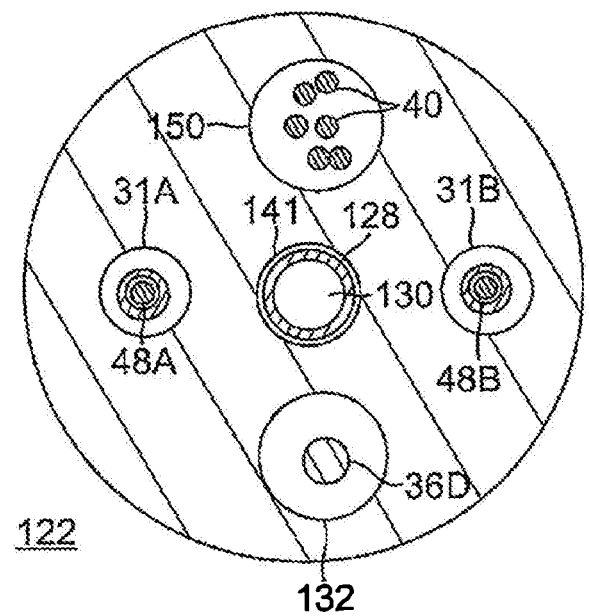
FIG. 10A is an end cross-sectional view of the distal tip of FIG. 10, taken along line A-A.
Figure 10B:
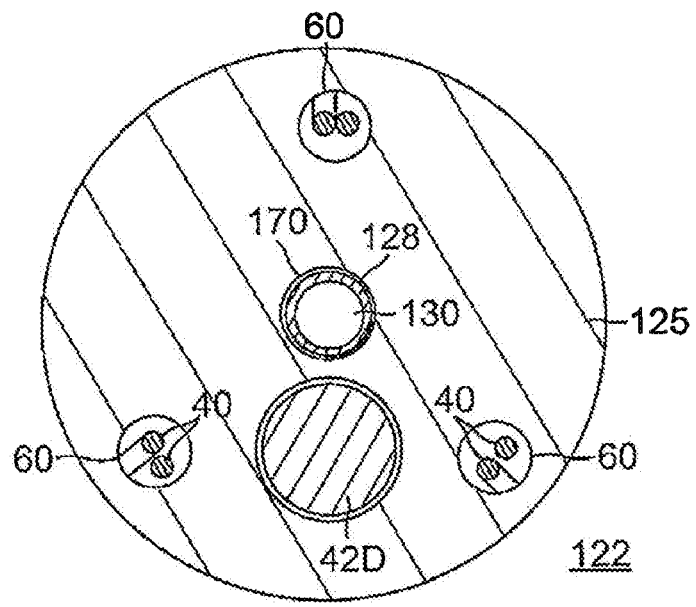
FIG. 10B is an end cross-sectional view of the distal tip of FIG. 10, taken along line B-B.

The distal tip 22 may carry any number of microelectrodes 26. For example, the distal tip 22 may carry 16 microelectrodes 26 (eight distal and eight radial), as shown in FIG. 8, or it may carry six microelectrodes 26 (three distal and three radial), as shown in FIG. 9. With reference to FIGS. 9 and 10, a distal portion of a focal catheter 100 is shown, with a distal tip 122 that extends from a deflection section 114. With additional reference to FIGS. 10A and 10B, the distal tip 122 constructed in a similar manner described above for distal tip 22, including a nonmetallic, electrically insulating substrate body 125 and a plurality of surface-embedded radial and distal microelectrodes 26R and 26D whose outer surfaces 63R and 63D, respectively, are generally flush with outer surface 133 of the substrate body 125 to present a generally smooth, atraumatic distal tip profile. The substrate body 125 has similar axial and radial passages 160 and 162 for the lead wires and indentations 164 for the embedded microelectrodes. A distal location sensor 142D is located in a blind hole 51 formed in the proximal end of the substrate body 125. However, in this embodiment, the focal catheter 100 is configured with a guide wire passage 130 that extends longitudinally within the catheter from the control handle 16 to the distal tip 122. The passage 130 is defined by the lumen of a tubing 128 that extends through the control handle, the center lumen of the catheter body, a dedicated on-axis lumen 141 in the deflection section 114, and a connector tubing 134 connecting the deflection section 114 and the distal tip 122. A distal end of the tubing 128 is received in a longitudinal on-axis passage 170 formed the substrate body 125 to extend the guidewire passage 130 to the distal face of the substrate body.

The focal catheter 100 may be deflected bi-directionally by means of first and second puller wires 48A and 48B extending through diametrically opposite, off axis lumens 31A and 31B formed in the tubing of the deflection section 114.

To use the catheter 100 of the invention, an electrophysiologist introduces a dilator and a guiding sheath into the patient, as is generally known in the art. A suitable guiding sheath for use in connection with the inventive catheter is the PREFACE™ Braided Guiding Sheath (commercially available from Biosense Webster, Inc., Irvine, Calif.). The catheter is introduced through the guiding sheath with the expander extended and the basket assembly collapsed so that the basket assembly can be fed into the guiding sheath. The guiding sheath covers the spines of the basket assembly in a collapsed position so that the entire catheter can be passed through the patient's vasculature to the desired location. Once the basket assembly of the catheter reaches the desired location, e.g., the left atrium, the guiding sheath is withdrawn to expose the basket assembly. The expander is drawn proximally or otherwise manipulated so that the spines flex outwardly. With the basket assembly radially expanded, the ring electrodes contact atrial tissue. Using the ring electrodes on the spines in combination with the location sensor(s), the electrophysiologist can map local activation time and/or ablate and irrigate as needed, in diagnosing and providing therapy to the patient. With the multiple electrodes on the basket assembly, the catheter enables the electrophysiologist to obtain a true anatomy of a cavernous region of the heart, including an atrium, by measuring more points than with traditional catheters, allowing him to map the region more quickly. Moreover, for focal tissue contact, the electrophysiologist can direct the distal tip with high density microelectrodes for greater location precision and greater sensitivity in detecting more subtle electrical activity of heart tissue.

The preceding description has been presented with reference to presently disclosed embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale and any feature(s) of an embodiment may be incorporated into any other embodiments or combined with any other feature(s) of another embodiment, as desired or needed. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
   an elongated catheter body having proximal and distal ends and at least one lumen therethrough;
   a tip assembly at the distal end of the catheter body, the tip assembly comprising:
      a substrate body having proximal and distal portions and a solid and unitary construction, the proximal portion of the substrate body comprising a proximal outer surface having a two-dimensional curvature, and the distal portion of the substrate body comprising a distal outer surface having a three-dimensional curvature,
      a plurality of first recessed microelectrodes embedded in the proximal outer surface so that the first recessed microelectrodes have a first microelectrode curvature that generally conforms to the two-dimensional curvature of the proximal outer surface of the substrate body,
      a plurality of second recessed microelectrodes embedded in the distal outer surface so that the second recessed microelectrodes have a second microelectrode curvature that generally conforms to the three-dimensional curvature of the distal outer surface of the substrate body,
      a plurality of microelectrode lead wires, each of the microelectrode lead wires corresponding to one of the plurality of first recessed microelectrodes or the plurality of second recessed microelectrodes, and
      at least first and second isolated through holes in the solid construction of the substrate body, at least one of the plurality of microelectrode lead wires extending from the respective first or second recessed microelectrode through the first isolated through hole to a proximal end of the substrate body, and at least one other of the plurality of microelectrode lead wires extending from its respective first or second recessed microelectrode through the second isolated through hole to the proximal end of the substrate body.

2. The catheter of claim 1, wherein at least one of the plurality of first recessed microelectrodes has an outer surface flush with the proximal outer surface of the substrate body.

3. The catheter of claim 1, wherein at least one of the plurality of second recessed microelectrodes has an outer surface flush with the distal outer surface of the substrate body.

4. The catheter of claim 1, wherein at least one of the plurality of first recessed microelectrodes has an outer surface flush with the proximal outer surface of the substrate body, and at least one of the plurality of second recessed microelectrodes has an outer surface flush with the distal outer surface of the substrate body.

5. The catheter of claim 1, wherein each of the plurality of first recessed microelectrodes has a surface area of about 0.05 mm$^2$ to about 0.5 mm$^2$.

6. The catheter of claim 1, wherein each of the plurality of second recessed microelectrodes has a surface area of about 0.05 mm$^2$ to about 0.5 mm$^2$.

7. The catheter of claim 1, wherein each of the plurality of first recessed microelectrodes has a surface area of about 0.05 mm$^2$ to about 0.5 mm$^2$, and each of the plurality of second recessed microelectrodes has a surface area of about 0.05 mm$^2$ to about 0.5 mm$^2$.

8. The catheter of claim 1, wherein each of the first recessed microelectrodes has a surface area of about 0.015 mm$^2$.

9. The catheter of claim 1, wherein each of the second recessed microelectrodes has a surface area of about 0.015 mm$^2$.

10. The catheter of claim 1, wherein each of the first recessed microelectrodes has a surface area of about 0.015 mm$^2$, and each of the second recessed microelectrodes has a surface area of about 0.015 mm$^2$.

11. A catheter comprising:
   an elongated catheter body having proximal and distal ends and at least one lumen therethrough;
   a tip assembly at the distal end of the catheter body, the tip assembly comprising:
      a substrate body having proximal and distal portions and a solid and unitary construction, the proximal portion of the substrate body comprising a proximal outer surface having a two-dimensional curvature, and the distal portion of the substrate body comprising a distal outer surface having a three-dimensional curvature,
      two to ten first recessed microelectrodes embedded in the proximal outer surface so that the first recessed microelectrodes have a first microelectrode curvature that generally conforms to the two-dimensional curvature of the proximal outer surface of the substrate body, each of the first recessed microelectrodes having a surface area of about 0.05 mm$^2$ to about 0.5 mm$^2$,
      two to ten second recessed microelectrodes embedded in the distal outer surface so that the second recessed microelectrodes have a second microelectrode curvature that generally conforms to the three-dimensional curvature of the distal outer surface of the substrate body, each of the second recessed microelectrodes having a surface area of about 0.05 mm$^2$ to about 0.5 mm$^2$,
      a plurality of microelectrode lead wires, each of the microelectrode lead wires corresponding to one of the first or second recessed microelectrodes, and
      at least first and second isolated through holes in the solid construction of the substrate body, at least one of the plurality of microelectrode lead wires extending from the respective first or second recessed microelectrode through the first isolated through hole to the proximal end of the substrate body, and at least one other of the plurality of microelectrode lead wires extending from its respective first or second recessed microelectrode through the second isolated through hole to the proximal end of the substrate body.

12. The catheter of claim 11, wherein each of the first recessed microelectrodes has a surface area of about 0.015 mm$^2$.

13. The catheter of claim 11, wherein each of the second recessed microelectrodes has a surface area of about 0.015 mm$^2$.

14. The catheter of claim 11, wherein each of the first recessed microelectrodes has a surface area of about 0.015 mm$^2$, and each of the second recessed microelectrodes has a surface area of about 0.015 mm$^2$.

15. The catheter of claim 11, wherein the two to ten first recessed microelectrodes comprises at least eight microelectrodes.

16. The catheter of claim 11, wherein the two to ten second recessed microelectrodes comprises at least eight microelectrodes.

17. The catheter of claim 11, wherein the two to ten first recessed microelectrodes comprises at least eight microelectrodes, and the two to ten second recessed microelectrodes comprises at least eight microelectrodes.

18. The catheter of claim 11, wherein the two to ten first recessed microelectrodes comprises at least three microelectrodes.

19. The catheter of claim 11, wherein the two to ten second recessed microelectrodes comprises at least three microelectrodes.

20. The catheter of claim 11, wherein the two to ten first recessed microelectrodes comprises at least six microelectrodes, and the two to ten second recessed microelectrodes comprises at least three microelectrodes.

* * * * *